United States Patent [19]
Cumings

[11] Patent Number: 6,154,522
[45] Date of Patent: Nov. 28, 2000

[54] METHOD, SYSTEM AND APPARATUS FOR AIMING A DEVICE EMITTING A RADIANT BEAM

[75] Inventor: Robert C. Cumings, St. Peters, Mo.

[73] Assignee: McDonnell Douglas Corporation, St. Louis, Mo.

[21] Appl. No.: 09/248,855

[22] Filed: Feb. 11, 1999

[51] Int. Cl.[7] ..................................................... A61B 6/08
[52] U.S. Cl. .......................... 378/206; 378/205; 356/138
[58] Field of Search ..................................... 378/206, 205, 378/204, 162, 68; 356/121, 123, 138, 139.1, 153

[56] References Cited

U.S. PATENT DOCUMENTS

| | | | |
|---|---|---|---|
| 4,887,286 | 12/1989 | Seidenberg | 378/170 |
| 5,024,528 | 6/1991 | Freund et al. | 356/356 |
| 5,031,203 | 7/1991 | Trecha | 378/205 |
| 5,077,905 | 1/1992 | Murray, Jr. | 33/412 |
| 5,084,980 | 2/1992 | Skopec et al. | 33/286 |
| 5,177,779 | 1/1993 | Cornu et al. | 378/206 |
| 5,274,433 | 12/1993 | Madey et al. | 356/155 |
| 5,402,577 | 4/1995 | Cumings | 33/286 |
| 5,537,453 | 7/1996 | Williams et al. | 378/206 |
| 5,598,269 | 1/1997 | Kitaevich et al. | 356/399 |
| 5,644,616 | 7/1997 | Landi et al. | 378/206 |
| 5,661,775 | 8/1997 | Cramer et al. | 378/206 |
| 5,680,698 | 10/1997 | Armington et al. | 29/833 |
| 5,689,545 | 11/1997 | Hopkins | 378/206 |
| 5,707,360 | 1/1998 | Röckseisen | 604/116 |
| 5,760,872 | 6/1998 | Reis et al. | 351/205 |
| 5,773,721 | 6/1998 | Bashyam | 73/596 |

*Primary Examiner*—David P. Porta
*Attorney, Agent, or Firm*—Bryan Cave LLP

[57] ABSTRACT

The present invention is a method, system and apparatus for aiming an x-ray system at the surface of a target object, such that the x-ray beam will strike the surface of the target object at a predetermined angle and direction. A laser is positioned on the surface of the target object, such that the linear beam of light emitted from the laser forms an angle with respect to the surface of the target object corresponding to the predetermined angle and direction at which the x-ray beam is desired to strike the surface of the target object. A mirror is placed on the lens of the x-ray tube. The x-ray lens and the object are then configured such that the laser beam strikes the mirror and is reflected back to the point of origin. The x-ray device is thus aimed such that, when energized, the x-ray beam will strike the surface of the target object at the predetermined angle and direction.

24 Claims, 2 Drawing Sheets

METHOD, SYSTEM AND APPARATUS FOR AIMING A DEVICE EMITTING A RADIANT BEAM

BACKGROUND OF THE INVENTION

1. Field of the Invention

The present invention pertains to the aiming of equipment producing radiant beams.

2. Background

Radiography is a technique for producing an image of an opaque object by transmitting radiation, such as an x-ray or gamma-ray beam, through the target object onto adjacent radiographic film. In addition to medical applications, radiography has been used to inspect the internal characteristics of objects in nondestructive inspection procedures. Radiographic imaging is used to identify internal damage, flaws and material anomalies without destroying the object inspected. Radiographic inspection is used in many industrial applications including, for example, production and testing of pipelines and boilers, production and inspection of nuclear equipment, shipbuilding and maintenance, aviation and aerospace, electrical engineering and electronics production and maintenance, metal casting, and automotive applications. Radiographic inspection is described in Cumings U.S. Pat. No. 5,402,577, which is incorporated herein by reference in its entirety.

The usefulness of a radiographic image often depends on the angle and direction at which the radiant beam strikes the target object to be inspected. For example, it is often desirable to produce a radiographic image of an object that shows an internal void between parallel structural members or materials (such as a honeycomb core). Such an image can be produced only if the radiant beam strikes the surface of the target object at an angle and direction that allows the radiation to pass through the internal void of the target object. Internal structural members, such as structural members forming a honeycomb core, frequently do not form a perpendicular angle with respect to the surface skin of a part. Hence, aiming a radiographic transmission machine so that the radiant beam strikes the surface skin of the target object at a perpendicular angle will not always produce a radiographic image allowing for adequate inspection of the interior void between internal structural members. To produce a radiographic image allowing inspection of the interior void of such a target object, the radiographic transmission device must be aimed so that the central ray of the transmitted beam strikes the surface of the target object, and passes through the target object, at a direction and angle substantially the same as the angle and direction that the interior structural member forms with the interior wall of the part. Directing the radiographic beam at such an angle and direction allows the beam to pass through the internal void of the part without passing through any structural members. This is just an example of the need for alignment of a radiant beam. Of course, objects having irregular shaped interior structures, or interior structural members which do not abut against the interior wall of the target object, may also require special alignment of the radiant beam for proper radiographic inspection.

Transmission systems typically used for the radiographic inspection allow the operator to aim the beam so that the beam can be passed through the target object at a desired direction and angle. One type of transmission system, an x-ray system, generally comprises an x-ray tube having a lens from which the x-ray beam is emitted. The tube is sometimes mounted to either a portable or stationary tube stand and is attached to a controller through which the operator can control and manipulate the position (angle) and orientation (direction) of the transmission source. For inspection of large parts, the part typically remains stationary and the x-ray lens is manipulated to aim the x-ray beam at the part to be inspected.

Because radiant beams are often invisible, the operator ordinarily must use some visible means to ascertain the angle and location at which the radiant beam will pass through the target object to be inspected. For example, in older x-ray systems, the x-ray beam was aimed through the use of a mechanical rod, which was extended between the desired location on the part to be inspected to the center of the x-ray lens. In this manner, the mechanical rod provided a visual representation of the angle, direction and location that the central ray of the x-ray beam would pass through the target object to be inspected. Such mechanical aiming systems are cumbersome and inaccurate, and have generally been replaced with laser light aiming devices, which are now commonly used for positioning various types of radiographic equipment. For example, prior use of a laser beam for orienting and aiming of an x-ray machine for medical applications is described in Cramer et al. U.S. Pat. No. 5,661,775 and Williams et al. U.S. Pat. No. 5,537,453. Prior art laser aiming devices generally operate under the same principle as prior art mechanical aiming devices. Generally, laser aiming devices have heretofore directed a visible laser beam coaxial with the central ray of the x-ray beam, giving a visual indication of the point at which the central ray will strike and pass through the target object.

One shortcoming of prior art laser aiming systems is that, while they generally provide an indication of the location that the central ray of the beam will strike the target object to be inspected, they do not provide an accurate visual indication of the angle and direction at which the beam will strike and pass through the target object. Until now, x-ray operators using conventional laser aiming devices have had no alternative but to use trial and error in order to seek to properly angle and direct the beam with respect to the target object to be inspected. Through the repetitive trial and error process, the x-ray operator aligns the x-ray machine using the laser, and then energizes the x-ray machine to produce an image on radiographic film. The operator then inspects the image to determine if the image was taken at the desired angle. If not, the operator then must adjust the angle of the x-ray lens and retake the image. This iterative process must be repeated until the operator produces an acceptable image at the desired angle and direction. This trial and error method is extremely expensive, time consuming and may result in poor quality inspections.

In many instances the desired angle at which the radiant beam should strike and pass through the outer surface of the target object can be predetermined. Thus, there is a substantial need for a method, system and apparatus, that will allow a radiant beam emitter to be aimed at a target object such that the radiant beam strikes the surface of the target object at the predetermined angle and direction. Such a method, system and apparatus will, among other advantages, eliminate the substantial time and expense associated with trial and error methods heretofore used with conventional laser aiming devices.

SUMMARY OF THE INVENTION

The present invention is directed to a method, system and apparatus for aiming a radiant beam emitter at a target object, such that the radiant beam strikes the surface of the target object at a predetermined angle and direction.

In accordance with one preferred embodiment of the present invention, a light emitter is preferably positioned on the surface of the target object such that a beam of light forms an angle with respect to the surface of the target object corresponding to the predetermined angle and direction at which the radiant beam is desired to strike the surface of the target object. A reflector having a planar surface is preferably positioned on the radiant beam emitter such that, when the radiant beam emitter is energized, the radiant beam strikes the reflector at a substantially perpendicular angle to the planar surface of the reflector. The target object and the radiant beam emitter are preferably positioned such that the beam of light strikes the reflector and is reflected substantially back to its point of origin.

In one preferred embodiment, the beam of light comprises a laser beam and the reflector comprises a mirror.

In one preferred embodiment, the reflector and the radiant beam emitter are positioned such that the radiant beam strikes the reflector substantially at the center point of the reflector. The target object and the radiant beam emitter are preferably positioned such that the beam of light strikes the reflector substantially at the center point of the reflector and is reflected back to the point of origin.

In accordance with another aspect of a preferred embodiment of the invention, the radiant beam emitter is an x-ray device and the radiant beam is an x-ray beam emitted from the x-ray device.

A radiographic image of a target object taken at a predetermined angle and direction is produced in accordance with another aspect of the present invention. A light emitter is preferably positioned on the surface of the target object, such that the beam of light forms an angle with respect to the surface of the target object corresponding to the predetermined angle and direction at which the radiographic image is desired to be produced. A reflector having a planar surface is preferably positioned on a radiant beam emitter such that, when the radiant beam emitter is energized, a radiant beam strikes the reflector at a substantially perpendicular angle to the planar surface of the reflector. The target object and the radiant beam emitter are preferably positioned such that the beam of light strikes the reflector and is reflected substantially back to the point of origin. A radiographic material is preferably positioned such that when the radiant beam emitter is energized the radiant beam impinges the radiographic material after passing through the target object, thereby producing the radiographic image of the target object.

Another aspect of a preferred embodiment of the present invention encompasses a light directing apparatus adapted to direct a linear beam of light at a predetermined angle and direction. One embodiment of the apparatus preferably comprises a light emitter adapted to emit the linear beam of light and a casing adapted to direct the beam of light. The casing preferably has an upper portion, a lower portion and an axis. The upper portion preferably has a planar upper surface. The lower portion preferably has a planar lower surface. The upper portion and the lower portion are preferably angularly separated with respect to a cross-sectional plane perpendicular to the axis. The upper and lower portion are preferably connected at the angular separation such that each portion may be independently rotated about the axis. The light emitter is preferably disposed in the upper portion of the casing such that the light emitter is positioned to emit a beam of light at an angle that is substantially perpendicular to the planar upper surface of the casing. The upper and lower portions can preferably be rotationally adjusted so as to direct the linear beam of light at a predetermined angle and direction with respect to the planar lower surface of the light directing apparatus.

Preferably, the casing further comprises corresponding indexing marks, or other indexing or measuring means, on the upper and lower portions to calibrate, determine, adjust, and/or indicate the angle of the beam of light with respect to the planar lower surface of the light directing apparatus.

The described method, system and apparatus of the present invention provide a new, useful and highly effective and efficient means for aiming a radiant beam emitter at a target object such that the radiant beam strikes the surface of the target object at the predetermined angle and direction. The invention described herein, among its many advantages, saves time and expense over the trial and error method heretofore used with conventional laser aiming devices, and results in more accurate radiographic images.

DRAWINGS

These, and other features, aspects and advantages of the present invention will become more fully apparent from the following detailed description, appended claims, and accompanying drawings where:

DETAILED DESCRIPTION OF THE INVENTION

Figure 1A:
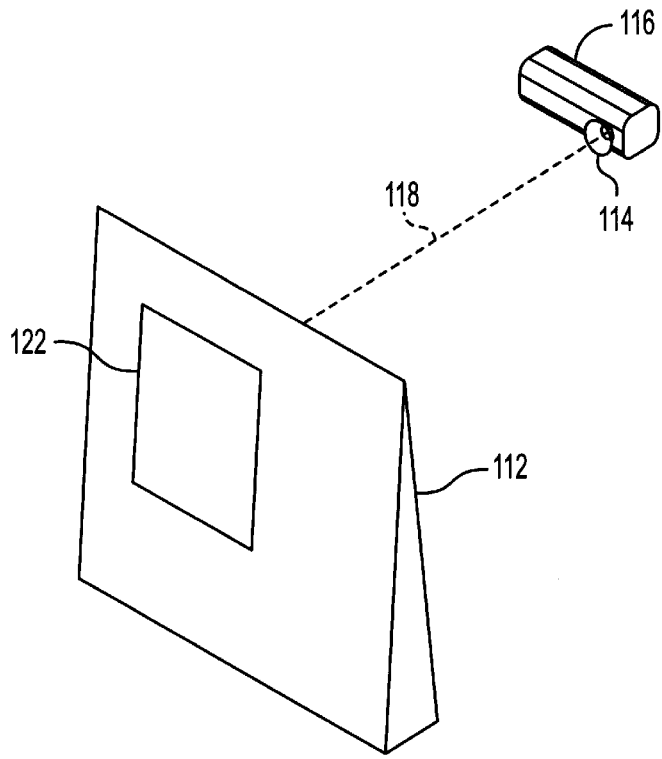
FIG. 1A is a perspective view of one preferred embodiment of the method and system of the present invention viewed from the back of the target object.
Figure 1B:
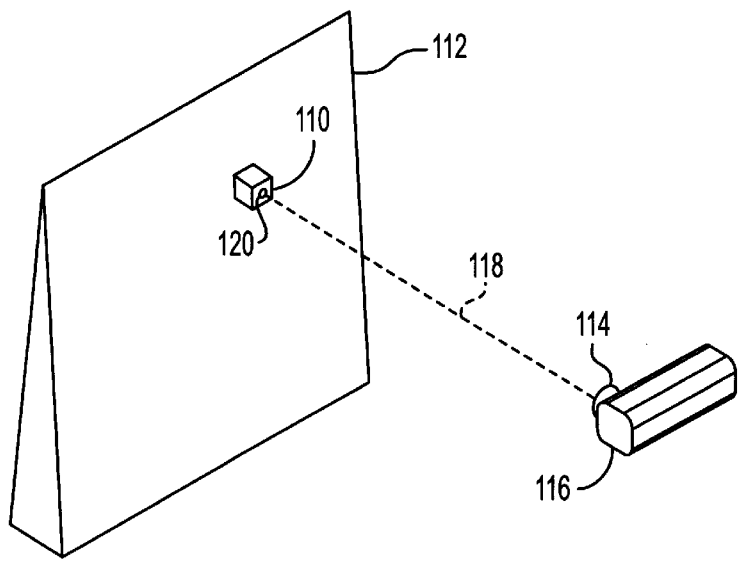
FIG. 1B is a perspective view of one preferred embodiment of the method and system of the present invention viewed from the front surface of the target object.

As shown in FIGS. 1A and 1B, one preferred method and system of the present invention for aiming a radiant beam emitter 116 at a target object 112 having a surface, principally comprises a light emitter 110 adapted to emit a beam of light 118 from a point of origin 120 positioned on the target object 112 and a reflector 114 positioned on the radiant beam emitter 116. The light emitter 110 is preferably positioned on, or in close proximity to, the surface of the target object 112. The beam of light 118 is preferably linear and is preferably emitted in a direction and at an angle relative to the surface of the target object 112 corresponding to the predetermined angle and direction at which the radiant beam is desired to strike the surface of the target object 112. The reflector 114, preferably having a planar surface thereon, is preferably positioned on the radiant beam emitter 116 such that, if energized, the radiant beam would strike the reflector 114 preferably at the center point of the reflector at an angle perpendicular to the planar surface of the reflector 114. The target object 112 and the radiant beam emitter 116 are then positioned such that the beam of light 118 strikes the reflector 114, preferably at the center point of the reflector, and is reflected substantially back to the point of origin 120. When the radiant beam emitter 116 is energized, the beam will preferably strike the surface of the target object 112 at the predetermined angle and direction.

In one preferred embodiment, the radiant beam emitter 116 is an x-ray system for radiographic inspection of objects, such as pipelines and boilers, production and inspection of nuclear equipment, shipbuilding and maintenance, aviation and aerospace, electrical engineering and electronics production and maintenance, metal casting, and automotive applications. Such systems typically have an x-ray tube with an x-ray lens from which an x-ray beam is emitted. The x-ray tube is sometimes mounted to a tube stand. The x-ray system preferably has a control mechanism for x-ray source manipulation, which allows the position (angle) and orientation (direction) of the x-ray source to be adjusted so as to aim the beam at the target object. The x-ray system may be stationary or portable. However, the term "radiant beam emitter" is and shall be construed broadly to include any device, mechanism or apparatus that emits or propagates waves or particles, such as, light, sound, radiant heat or other waves or particles. The radiant beam emitter may include, for example, x-ray, gamma-ray, or ultrasonic equipment used for industrial, medical or dental applications.

Preferably, the central axis of the radiant beam is aimed at the target object. The central axis of the radiant beam is the center or focal point of the beam, for example the central ray of an x-ray beam. The central ray of an x-ray beam emitted by an x-ray machine is usually the strongest of the many rays typically emitted in conical fashion, from the lens of the x-ray tube.

The target object 112 at which the beam is directed may be any object for which it is desirable to aim a radiant beam at the surface of the object at a predetermined angle and direction. For example, the target object may be an object, such as an aircraft part, for which nondestructive inspection is desired. In one example, one preferred embodiment of the present invention may be used to aim an x-ray system to nondestructively inspect the internal honeycomb structure of an aircraft part by producing a radiographic image of the internal structure of the part taken at a desired angle of view. Those skilled in the art will fully appreciate that the target object at which the beam is directed may be any variety of things, including, for example: pipelines; boilers; nuclear equipment; shipbuilding equipment; aviation and aerospace equipment; automotive equipment; electrical and electronic equipment; metal casting; and, in medical applications, parts of the human or animal anatomy.

The light emitter 110 may be any device that produces a beam of light. Preferably, the beam of light is a linear beam of light. For example, the device may preferably be a laser that emits a visible laser beam. In one preferred embodiment the laser is a low power visible laser. Safety to operators is a primary consideration in limiting the power of the laser. In a preferred embodiment, the device that produces the linear beam of light is a 9 volt battery powered class II diode laser. The diode laser is preferably aligned prior to use to ensure that the laser beam emitted from the device is linear.

In a preferred embodiment, where the present invention is used to direct a radiant beam at the surface of a target object 112 such that the beam will strike the surface of the target object 112 at an angle substantially perpendicular to the surface of the target object 112, the light emitter 110 is preferably disposed within a structure preferably having a planar back surface. The back surface of the structure is preferably placed against the surface of the target object 112. A beam of light is preferably emitted from the light emitter 110 at an angle perpendicular to the front surface of the target object 112. The planar back surface of the structure may preferably be attached to the surface of the target object 112 substantially at the point at which the radiant beam is desired to strike the target object 112 using any number of detachable means which are well known in the art such as, for example, double back tape. By attaching the structure to the target object 112 in this manner, the beam of light 118 is preferably directed away from the target object 112 at a substantially perpendicular angle with respect to the surface of the target object 112.

Figure 2A:
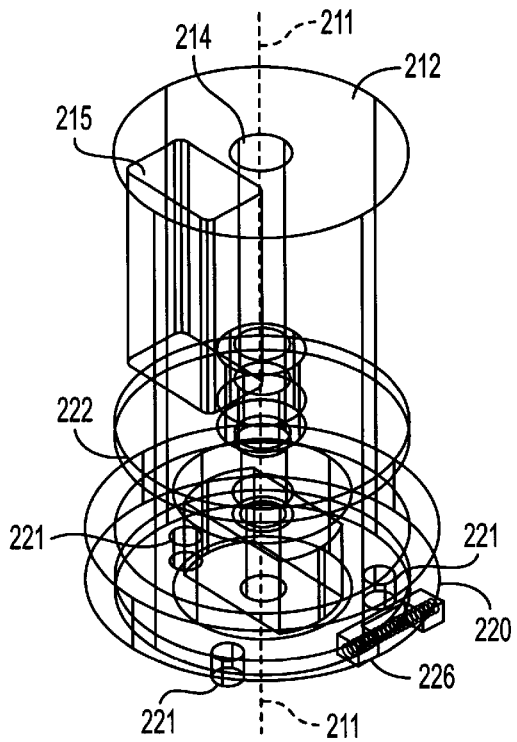
FIG. 2A is a sectional perspective view of one preferred embodiment of a light directing apparatus of the present invention.
Figure 2B:
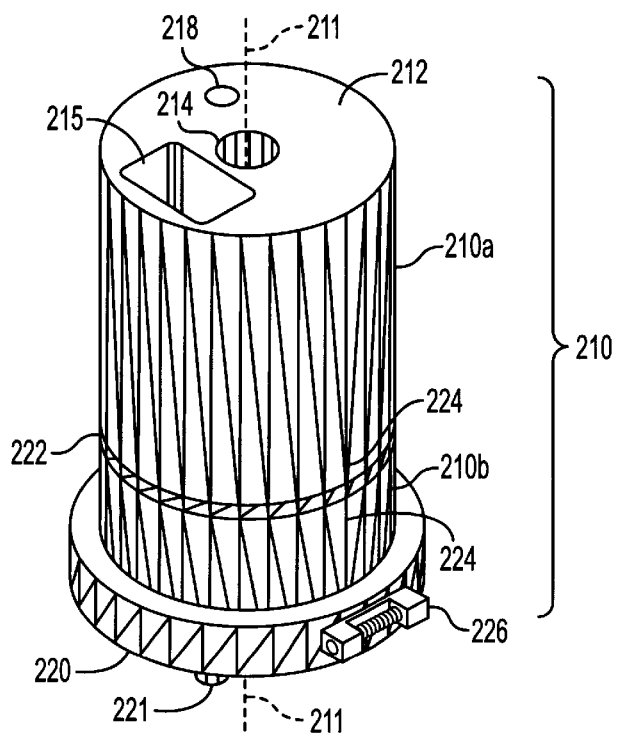
FIG. 2B is a perspective view of one preferred embodiment of a light directing apparatus of the present invention.

In another preferred embodiment, the light emitter 110 is preferably housed in a light directing apparatus illustrated in FIGS. 2A and 2B, where the present invention is used to direct a radiant beam at the surface of a target object 112 such that the radiant beam will strike the surface of the target object 112 at a predetermined angle and direction. The light directing apparatus allows a linear beam of light to be directed from the surface of the target object 112 at a predetermined angle and direction. Referring now to FIGS. 2A and 2B, the light directing apparatus preferably comprises a casing 210. In one preferred embodiment, the casing 210 is cylindrical. The casing preferably has an upper portion 210a, a lower portion 210b and an axis 211. The upper portion 210a of the casing 210 preferably has a planar upper surface 212. In one preferred embodiment, the upper portion 210a of the casing 210 has an axial orifice 214 through the center of the casing in which a light emitter 110 is inserted. As will be recognized by those skilled in the art, numerous types of light sources may be used in the present invention, including, for example, a battery-operated class II laser diode. The upper portion 210a preferably further comprises, in one preferred embodiment, a second orifice 215 for housing an energy source, such as a battery, to power the light emitter 110. The light directing apparatus preferably has a power switch 218 for energizing the light source 110. The lower portion 210b preferably has a planar lower surface 220 adapted to be positioned upon the surface of the target object. The lower surface 220 of the casing 210 preferably has removable feet 221 to facilitate positioning on the surface of the target object if desired, or such other means to place or affix the light directing apparatus to the target object as will be known or obvious to those skilled in the art. The upper portion 210a and the lower portion 210b of the casing 210 are preferably angularly separated with respect to a cross-sectional plan perpendicular to the axis 211 of the casing 210. This angular separation 222 may, in one preferred embodiment, be achieved by cutting a casing into two parts at an angle of approximately 1° to 45° with respect to a cross-sectional plane perpendicular to the axis of the cylinder. For example, in one embodiment, the angular separation is achieved by cutting a casing into two parts at an angle of approximately 10° with respect to a cross-sectional plane perpendicular to the axis of the cylinder, allowing the light directing apparatus to direct the beam of light at angles from 80° to 90° with respect to the planar lower surface of the apparatus. The upper portion 210a and lower portion 210b of the casing 210 are preferably attached at the angular separation 222 such that each portion can be separately rotated about the axis 211. The apparatus preferably has corresponding indexing marks 224 with numerical indicators on the upper 210a and lower 210b portions, which indicate the angle of the beam of light with respect to the plane formed by the lower surface 220. In other preferred embodiments, the apparatus may have other indexing or measuring means, on the upper 210a and lower 210b portions to calibrate, determine, adjust, and/or indicate the angle of the beam of light with respect to the planar lower surface 220 of the light direction apparatus. The light directing apparatus preferably further comprises one or more leveling indicators 226 to aid in positioning the apparatus.

The light directing apparatus illustrated in FIGS. 2A and 2B is operated by positioning the planar lower surface 220 against the surface of the target object at which the radiant beam will be directed. The upper portion 210a of the casing is then rotated while the lower portion 210b is held stationary such that linear beam of light can be directed at a desired angle and direction with respect to the surface of the target object. By using the corresponding indexing marks 224 on the upper and lower casing, the light directing apparatus can be adjusted to direct the beam of light from the surface of the target object at a predetermined angle and direction.

Referring again to FIGS. 1A and 1B, the reflector 114, in one preferred embodiment, is a mirror preferably having a planar surface. In one preferred embodiment, the mirror is attached to the x-ray lens of an x-ray tube. The mirror may preferably be removed prior to energizing the radiant beam emitter or it may be left on the radiant beam emitter and the radiant beam passed through the mirror. Those skilled in the art will recognize that the reflector 114 need not necessarily be a mirror. Any reflective device may be used that is preferably capable of reflecting a linear beam of light such that when the beam of light strikes the surface of the reflector at a perpendicular angle, the beam is reflected substantially back to its point of origin.

The invention will be further clarified by consideration of the following example, which is intended to be purely exemplary of the use of the invention. The system and method of the present invention are described in this example as used for radiographic inspection of an aircraft part. In this example, it is desired that an x-ray beam strike the surface of a part to be inspected from a predetermined direction and at a predetermined angle of 45° with respect to the surface of the part to produce a radiographic image of the inner structure of the part from this predetermined direction and angle. With reference to FIGS. 1A, 1B, 2A and 2B, the target object 112 (in this example, the part to be inspected) is positioned in front of the radiant beam emitter 116 (in this example, an x-ray device) and radiographic film 122 is placed behind the part. Using the corresponding indexing marks 224 on the light directing apparatus illustrated in FIGS. 2A and 2B, the upper portion 210a and lower portion 210b of the casing 210 are rotationally adjusted such that the beam of light 118 is emitted at an angle of 45° with respect to the plane of the lower surface 220 of the light directing apparatus. The lower surface 220 of the light directing apparatus is then placed against the surface of the target object 112 at the point at which the radiographic image is to be taken. The light emitter 110 is then energized and the linear beam of light 118 is directed from the apparatus at a 45° angle with respect to the surface of the target object 112. The light directing apparatus is then and rotationally adjusted so that the beam of light 118 is emitted in a direction corresponding to the desired direction that the image is to be taken. The reflector 114 (in this example, a planar mirror) is placed over the lens of the x-ray tube. The lens of the x-ray tube is then positioned with respect to the target object 112 such that the linear beam of light 118 strikes the surface of the reflector 114 and is directed back to the point of origin 120. The target object 112 and the x-ray lens are thus positioned such that when the x-ray system is energized, the central ray of the x-ray beam will travel in coaxial alignment with the path of the beam of light, thus striking and passing through the part at the predetermined angle and direction. The light directing apparatus and the mirror may then removed. The x-ray system may then be energized to produce the internal image of the part at the desired angle and direction.

Though the present invention has been described with respect to certain presently preferred embodiments thereof, other embodiments will be apparent to those skilled in the art from consideration of the specification or practice of the invention disclosed herein. A principal use of the method, system and apparatus of the present invention is for radiographic inspection for a wide variety of industrial applications including, for example, production and testing of pipelines and boilers, production and inspection of nuclear equipment, shipbuilding and maintenance, aviation and aerospace, electrical engineering and electronics production and maintenance, metal casting, and automotive applications. Additional uses of the method system and apparatus of the present invention may include, for example, medical and dental applications, such as for the directing of x-ray equipment for radiographic imaging and treatment.

What is claimed is:

1. A method of aiming a radiant beam emitter at a target object having a surface, such that when the radiant beam emitter is energized the radiant beam strikes the surface of the target object at a predetermined angle and direction, the method comprising the steps of:

a) positioning on the surface of the target object a light emitter adapted to emit a beam of light from a point of origin, such that the beam of light forms an angle with respect to the surface of the target object corresponding to the predetermined angle and direction at which the radiant beam is desired to strike the surface of the target object;

b) positioning a reflector having a planar surface on the radiant beam emitter such that, when the radiant beam emitter is energized, the radiant beam strikes the reflector at a substantially perpendicular angle to the planar surface of the reflector; and c) positioning the target object and the radiant beam emitter such that the beam of light strikes the reflector and is reflected substantially back to the point of origin.

2. The method of claim 1 wherein the radiant beam emitter is an x-ray device and the radiant beam is an x-ray beam emitted from the x-ray device.

3. A method of aiming a radiant beam emitter at a target object having a surface, such that when the radiant beam emitter is energized, the radiant beam strikes the surface of the target object at an angle substantially perpendicular to the surface of the target object, the method comprising the steps of:

a) positioning on the surface of the target object a light emitter adapted to emit a beam of light from a point of origin, such that the beam of light forms a substantially perpendicular angle with respect to the surface of the target object;

b) positioning a reflector having a planar surface on the radiant beam emitter such that, when the radiant beam emitter is energized, the radiant beam strikes the reflector at a substantially perpendicular angle to the planar surface of the reflector; and c) positioning the target object and the radiant beam emitter such that the beam of light strikes the reflector and is reflected substantially back to the point of origin.

4. The method of claim 3 wherein the radiant beam emitter is an x-ray device and the radiant beam is an x-ray beam emitted from the x-ray device.

5. The method of claim 1 wherein the beam of light comprises a laser beam.

6. The method of claim 1 wherein the reflector comprises a mirror.

7. The method of claim 1 wherein the reflector has a center point, the reflector and the radiant beam emitter are positioned such that the radiant beam strikes the reflector substantially at the center point, and the target object and the radiant beam emitter are positioned such that the beam of light strikes the reflector substantially at the center point and is reflected back to the point of origin.

8. The method of claim 2 wherein the x-ray device comprises an x-ray tube having an x-ray lens from which the x-ray beam is emitted, and wherein the reflector is positioned over the x-ray lens.

9. A method of producing a radiographic image of a target object taken at a predetermined angle and direction, the method comprising the steps of:
   a) positioning on the surface of the target object a light emitter adapted to emit a beam of light from a point of origin, such that the beam of light forms an angle with respect to the surface of the target object corresponding to the predetermined angle and direction at which the radiographic image is desired to be produced;
   b) positioning a reflector having a planar surface on a radiant beam emitter such that, when the radiant beam emitter is energized, a radiant beam strikes the reflector at a substantially perpendicular angle to the planar surface of the reflector;
   c) positioning the target object and the radiant beam emitter such that the beam of light strikes the reflector and is reflected substantially back to the point of origin; and
   d) positioning a radiographic material adapted to receive a radiographic image such that when the radiant beam emitter is energized the radiant beam impinges the radiographic material after passing through the target object, thereby producing the radiographic image of the target object.

10. A system for aiming a radiant beam emitter at a target object having a surface, such that when the radiant beam emitter is energized a radiant beam strikes the surface of the target object at a predetermined angle and direction, the aiming system comprising:
   a) a light emitter adapted to emit a beam of light from a point of origin, the light emitter being positioned on the surface of the target object, such that the beam of light forms an angle with respect to the surface of the target object corresponding to the predetermined angle and direction at which the radiant beam is desired to strike the surface of the target object; and
   b) a reflector adapted to reflect the beam of light back to the point of origin, the reflector having a planar surface, the reflector being positioned on the radiant beam emitter such that, when the radiant beam emitter is energized, the radiant beam strikes the reflector at a substantially perpendicular angle to the planar surface of the reflector, the radiant beam emitter being positioned such that the reflector reflects the beam of light substantially back to the point of origin.

11. The system of claim 10 wherein the beam of light comprises a laser beam.

12. The system of claim 10 wherein the reflector comprises a mirror.

13. The system of claim 10 wherein the radiant beam emitter is an x-ray device and the radiant beam is an x-ray beam emitted from the x-ray device.

14. The system of claim 13 wherein the x-ray device comprises an x-ray tube having an x-ray lens from which the x-ray beam is emitted, and wherein the reflector is positioned over the x-ray lens.

15. A system for producing a radiographic image of a target object taken at a predetermined angle and direction, the system comprising:

a) a radiant beam emitter;
b) a light emitter adapted to emit a beam of light from a point of origin, the light emitter being positioned on the surface of the target object such that the beam of light forms an angle with respect to the surface of the target object corresponding to the predetermined angle and direction at which the radiographic image is desired to be produced;
c) a reflector having a planar surface, the reflector being positioned on the radiant beam emitter such that, when the radiant beam emitter is energized, a radiant beam strikes the reflector at a substantially perpendicular angle to the planar surface of the reflector, the radiant beam emitter being positioned such that the reflector reflects the beam of light substantially back to the point of origin; and
d) a radiographic material adapted to receive a radiographic image, the radiographic material being positioned such that the radiant beam impinges the radiographic material after passing through the target object, thereby producing the radiographic image.

16. A light directing apparatus adapted to direct a linear beam of light at a predetermined angle and direction, the light directing apparatus comprising:
   a) a light emitter adapted to emit the linear beam of light; and
   b) a casing adapted to direct the beam of light, the casing having an upper portion, a lower portion and an axis, the upper portion having a planar upper surface, the lower portion having a planar lower surface, the upper portion and the lower portion being angularly separated with respect to a cross-sectional plane perpendicular to the axis, the upper and lower portion being connected at the angular separation such that each portion may be independently rotated about the axis, the light emitter being disposed in the upper portion of the casing such that the light emitter is positioned to emit a beam of light at an angle that is substantially perpendicular to the planar upper surface of the casing, whereby the upper and lower portions can be rotationally adjusted so as to direct the linear beam of light at a predetermined angle and direction with respect to the planar lower surface.

17. The light directing apparatus of claim 16 wherein the casing further comprises corresponding indexing marks on the upper and lower portions to adjust and set the angle of the beam of light with respect to the planar lower surface of the light directing apparatus.

18. The light directing apparatus of claim 16 further comprising at least one leveling indicator disposed on the casing to level the light directing apparatus.

19. The method of claim 1 wherein the light emitter is disposed within a light directing apparatus comprising a casing adapted to direct the beam of light, the casing having an upper portion, a lower portion and an axis, the upper portion having a planar upper surface, the lower portion having a planar lower surface, the upper portion and the lower portion being angularly separated with respect to a cross-sectional plane perpendicular to the axis, the upper and lower portion being connected at the angular separation such that each portion may be independently rotated about the axis, the light emitter being disposed in the upper portion of the casing such that the light emitter is positioned to emit a beam of light at an angle that is substantially perpendicular to the planar upper surface of the casing, whereby the upper and lower portions can be rotationally adjusted so as to direct the linear beam of light at a predetermined angle and direction with respect to the planar lower surface.

20. The method of claim 19 wherein the casing further comprises corresponding indexing marks on the upper and lower portions to adjust and set the angle of the beam of light with respect to the planar lower surface of the light directing apparatus.

21. The method of claim 19 wherein the light directing apparatus further comprises at least one leveling indicator disposed on the casing to level the light directing apparatus.

22. The system of claim 10 wherein the light emitter is disposed within a light directing apparatus comprising a casing adapted to direct the beam of light, the casing having an upper portion, a lower portion and an axis, the upper portion having a planar upper surface, the lower portion having a planar lower surface, the upper portion and the lower portion being angularly separated with respect to a cross-sectional plane perpendicular to the axis, the upper and lower portion being connected at the angular separation such that each portion may be independently rotated about the axis, the light emitter being disposed in the upper portion of the casing such that the light emitter is positioned to emit a beam of light at an angle that is substantially perpendicular to the planar upper surface of the casing, whereby the upper and lower portions can be rotationally adjusted so as to direct the linear beam of light at a predetermined angle and direction with respect to the planar lower surface.

23. The system of claim 22 wherein the casing further comprises corresponding indexing marks on the upper and lower portions to adjust and set the angle of the beam of light with respect to the planar lower surface of the light directing apparatus.

24. The system of claim 22 wherein the light directing apparatus further comprises at least one leveling indicator disposed on the casing to level the light directing apparatus.

\* \* \* \* \*